(12) United States Patent
Mueller et al.

(10) Patent No.: US 9,097,569 B2
(45) Date of Patent: Aug. 4, 2015

(54) ULTRASONIC TRANSDUCER FOR USE IN A FLUID MEDIUM

(75) Inventors: Roland Mueller, Steinheim (DE); Gerhard Hueftle, Aspach (DE); Michael Horstbrink, Stuttgart-Feuerbach (DE); Tobias Lang, Stuttgart (DE); Sami Radwan, Stuttgart (DE); Bernd Kuenzl, Schwieberdingen (DE); Roland Wanja, Markgroening (DE)

(73) Assignee: ROBERT BOSCH GMBH, Stuttgart (DE)

( * ) Notice: Subject to any disclaimer, the term of this patent is extended or adjusted under 35 U.S.C. 154(b) by 315 days.

(21) Appl. No.: 13/520,962

(22) PCT Filed: Dec. 7, 2010

(86) PCT No.: PCT/EP2010/069037
§ 371 (c)(1),
(2), (4) Date: Sep. 28, 2012

(87) PCT Pub. No.: WO2011/085872
PCT Pub. Date: Jul. 21, 2011

(65) Prior Publication Data
US 2013/0014592 A1    Jan. 17, 2013

(30) Foreign Application Priority Data
Jan. 18, 2010  (DE) .......................... 10 2010 000 967

(51) Int. Cl.
*G01F 1/66* (2006.01)
*B06B 1/06* (2006.01)
*G01F 23/296* (2006.01)
*G01N 29/22* (2006.01)
*G01N 29/24* (2006.01)
*G10K 11/00* (2006.01)

(52) U.S. Cl.
CPC .............. *G01F 1/662* (2013.01); *B06B 1/0655* (2013.01); *G01F 23/296* (2013.01); *G01N 29/222* (2013.01); *G01N 29/2437* (2013.01); *G10K 11/004* (2013.01)

(58) Field of Classification Search
CPC ...................................................... G01F 1/662
USPC ................................... 73/592; 310/322, 326
See application file for complete search history.

(56) References Cited

U.S. PATENT DOCUMENTS

| 4,945,276 A | * | 7/1990 | Mylvaganam et al. | ........ 310/326 |
| 6,584,862 B1 | * | 7/2003 | Molenaar | ................... 73/861.27 |

FOREIGN PATENT DOCUMENTS

| DE | 29 34 031 | 10/1980 |
| DE | 83 37 585 | 6/1985 |

(Continued)

*Primary Examiner* — Hezron E Williams
*Assistant Examiner* — Mark A Shabman
(74) *Attorney, Agent, or Firm* — Kenyon & Kenyon LLP (57) ABSTRACT

An ultrasonic transducer for use in a fluid medium includes at least one housing, e.g., a sleeve, which has at least one interior space, and at least one transducer core having at least one electroacoustic transducer element is accommodated in the interior space. The housing has a housing wall at least partially enclosing the transducer core using at least one hollow space.

10 Claims, 4 Drawing Sheets

(56) References Cited

FOREIGN PATENT DOCUMENTS

| | | |
|---|---|---|
| DE | 87 12 391 | 1/1988 |
| DE | 38 26 799 | 2/1990 |
| DE | 101 58 015 | 6/2003 |
| DE | 10 2007 010 500 | 9/2008 |
| EP | 0 418 224 | 3/1991 |
| EP | 0 766 071 | 4/1997 |
| JP | 2002 135894 | 5/2002 |
| JP | 2002 214 008 | 7/2002 |
| WO | WO 88/08540 | 11/1988 |
| WO | WO 95/07529 | 3/1995 |

* cited by examiner

--Prior Art--

ULTRASONIC TRANSDUCER FOR USE IN A FLUID MEDIUM

BACKGROUND OF THE INVENTION

1. Field of the Invention

The present invention relates to an ultrasonic transducer for use in a fluid medium.

2. Description of the Related Art

Various types of ultrasonic transducers are known from the related art. By ultrasonic transducer one should generally understand, in this context, an element that is in a position to generate ultrasonic waves and/or pick up such ultrasonic waves and to convert them to electrical signals. Ultrasonic transducers are used, for instance, in fluid media for flow measurement, such as in the intake manifold or exhaust-gas tract of internal combustion engines, or in other fields of use, such as fluid-level sensors. Flow measurements may be undertaken, for example, by systems having two or more ultrasonic transducers, for instance, by evaluating running time differences. Examples of ultrasonic transducers are shown in published German patent application document DE 10 2007 010 500 A1, or in German patent applications DE 10 2008 055 123.6 and DE 10 2008 055 116.3, which are not believed to be prior art. Published Japanese patent application documents JP 2002 135894 A and JP 2002 214008 A also show corresponding ultrasonic transducers. In general, the ultrasonic transducers shown in the cited related art may also be modified according to the present invention within the scope of the present invention.

As a rule, known ultrasonic transducers have a transducer core having a piezoelement that is enclosed by a sleeve. On a radiation side, the ultrasonic transducer is in many cases closed by a sealing foil, as is described, for example in German patent applications DE 10 2008 055 116.3, in DE 10 2008 055 123.6 or in published Japanese patent application documents JP 2002 214008 A or JP 2002 135894 A.

In particular, during the manufacture of ultrasonic transducers having a sealing foil, but also in the case of other types of ultrasonic transducers, in practice, a multitude of technical challenges occurs. One technical challenge is particularly to ensure a secure and reliable fixing of the sealing foil. Especially, the mounting has to be assured in such a way that air occlusions are not able to lead to damage or reduction in quality of the ultrasonic transducer. A plurality of elements has to be particularly introduced into the inside of the housing sleeve, such as, in many cases, a damping encapsulation, wherein the insertion of the additional elements should not be able to impair the mounting quality of the foil.

BRIEF SUMMARY OF THE INVENTION

Therefore, an ultrasonic transducer is provided for use in a fluid medium, which solves the disadvantages of known ultrasonic transducers in a simple and reliable manner, and is especially in a position to ensure reliable sealing of the ultrasonic transducer at a simple mounting at the same time. The ultrasonic transducer is equipped for use in a fluid medium, particular a gas or a liquid, such as in air or an exhaust gas. The ultrasonic transducer may particularly be used for flow measurement, for instance, in the motor vehicle field.

The ultrasonic transducer includes at least one housing. This housing is particularly able to determine the outer shape of the ultrasonic transducer, in order to protect the ultrasonic transducer from mechanical effects from the outside. As will be presented in greater detail below, the housing may, for instance, be made wholly or partially of a metallic material, and/or of a plastic material. Composite materials are also conceivable. The housing may particularly be developed to be sleeve-shaped and/or may have radial symmetry with respect to an axis. The sleeve may be designed closed, for example, or completely or partially open.

The housing has at least one inside space, in which at least one transducer core is accommodated, having at least one electroacoustical transducer element. The internal space may be completely or partially locked, but preferably has an opening towards the fluid medium. The interior space may be situated cylindrically symmetrical or axially symmetrical to an axis of the ultrasonic transducer, for instance, an axis that runs perpendicularly to a radiation surface of the transducer core.

By an electroacoustic transducer element one should basically understand any element that is prepared to transform electrical signals to acoustical signals, especially to ultrasonic signals, or vice versa. In particular, this electroacoustic transducer element may include at least one piezoelectric transducer element. Without restriction of possible additional embodiments, the terms "piezo", "piezoceramic" or "piezoelectrical transducer" are therefore also used as synonyms for the electroacoustic transducer. However, the electroacoustic transducer may basically also include other types of electroacoustic transducer elements. Furthermore, the transducer may include additional elements besides the at least one electroacoustic transducer. For instance, an adaptation element may be provided, especially on a side of the electroacoustic transducer element facing the fluid medium. This at least one adaptation element, which may be designed as an adaptation layer, for example, especially as an impedance matching layer, may be equipped to improve an ultrasonic coupling between the electroacoustic and the fluid medium, particularly by impedance matching. Such adaptation elements are basically known from the related art, for instance, from the documents described above. Accordingly, we may, for example, refer the reader to this related art with respect to the construction and/or the design and/or the selection of materials for the optional adaptation elements. However, other designs are also possible. Moreover, the transducer elements may include additional elements. For instance, at least one compensating element may be provided, for example, a compensating element between the adaptation element and the electroacoustic transducer element. This compensating element, for example, at least one compensating layer, may be equipped, for instance, to compensate for thermomechanical stresses between the electroacoustic transducer element and the adaptation element. Thus, the adaptation element, as far as its material is concerned, is selected so that it has an impedance that lies between the acoustic impedance of the electroacoustic transducer element and the acoustic impedance of the fluid medium, optimally close to the geometric mean of these two impedances. Such adaptation elements may, however, have greatly different thermal expansions compared to the electroacoustic transducer element which, for example, may be compensated for by the compensating element. However, other designs not having a compensating element are basically also possible.

One idea of the present Application is particularly that the design and the construction of the ultrasonic transducer may be substantially improved, especially when taking into account the abovementioned technical challenges, if, instead of a simple housing, a hollow-walled housing is used. Accordingly, it is provided that one should design the housing in such a way that it has a housing wall enclosing the transducer core at least partially with at least one hollow space. This hollow space is preferably largely closed off by the outer region of the ultrasonic transducer outside the housing. Furthermore, the hollow space may be separately developed, completely or partially, from the interior space of the ultrasonic transducer. Basically, however, as will be described below, a connection may exist between the hollow space and the interior space, these spaces being able to be designed, however, as spaces that are geometrically separate from each other, but optionally being in connection. Preferably, the hollow space is, however, developed completely separately from an outer region of the ultrasonic transducer outside the housing.

The hollow space may particularly have one or more of the following hollow spaces: a hollow space formed by a flanging of the housing wall, particularly flanging towards the interior space of the housing; a hollow space subdivided by at least one rib, particularly a hollow space subdivided by a rib extending in the axial direction of the ultrasonic transducer; a bore hole running in the axial direction of the ultrasonic transducer; a hollow space annularly enclosing the interior space at least partially; a cored-out region running essentially annularly around the interior space; at least one hollowed-out region situated annularly; at least one hollow space formed by at least one radially running rib structure. Various exemplary embodiments of such hollow spaces will still be explained in greater detail. The at least one hollow space may particularly include a plurality of hollow spaces distributed essentially uniformly over the circumference of the housing wall.

The hollow space may be particularly designed in such a way that a wall thickness of the housing, particularly of the housing wall, varies over different regions of the housing by a factor of four, at a maximum. The cored-out regions and/or the hollowed-out regions which form the hollow space, for example, may extend so deeply into the sleeve that the resulting wall thicknesses over different sleeve regions vary by a factor of four at a maximum.

The hollow space may particularly be developed in such a way that an end face of the housing, facing the fluid medium, has a greater thickness in the radial direction of the ultrasonic transducer than an average wall thickness of the housing, especially a thickness of the housing wall. The embodiment of the hollow space may thus take place in such a way, for instance by an embodiment as a flanging, that the end face is embodied wider than the remaining housing wall. In this way, the end face may provide an increased adherence surface or other fixing surfaces and/or fixing contours, especially for fixing (e.g. adhering) a sealing foil, which will be explained in greater detail below.

The hollow space may be filled up entirely or partially by at least one functional element that is different from the material of the housing. By functional element, in this instance, one should basically understand any element which contributes in at least one way to the function of the ultrasonic transducer, with the exception of a purely static function, for instance, a housing function or a protective function. In this context, the functional element may be entirely or partially accommodated in the hollow space. The functional element may particularly include one or more of the following elements: a damping element, having at least one dampening material, which is designed to suppress structure-borne noise transmissions; a contact element for the electrical contacting of the electroacoustic transducer element; a holding element for holding a contact element for electrically contacting the electroacoustic transducer element; a screening element for screening electromagnetic effects on the interior space, especially a screening sheet metal.

The ultrasonic transducer may particularly be embodied so that the housing has at least one opening facing the fluid medium. This opening may be enclosed at least partially by an end face of the housing, particularly of the housing wall, for example circular ring-shaped or in the form of a polygonal ring. Within the opening there may be situated at least one radiation surface of the transducer core. By radiation surface one should understand the area of the transducer core, via which acoustic signals are able to be emitted to the fluid medium or acoustic signals are able to be picked up from the fluid medium. The radiation surface may be situated in one plane with the end face, in this instance, or may basically also be situated in another plane. A situation in the same plane is preferred, however. The openings and the end face may be covered partially by at least one sealing foil, in this instance. By sealing foil one should basically understand, within the scope of the present invention, any sealing element which, on one hand, permits an at least extensive decoupling of acoustic signals between the transducer core and the transducer housing, which, however, on the other hand, effects the sealing of the interior space. In particular, the sealing foil may be designed to keep away from the interior space, at least partially, thermal influences and/or chemical influences and/or pressure effects. The sealing foil may basically include a foil element, such as a plastic film and/or a metal foil. By a foil one should basically understand a flexible element, which has a thickness that lies at least one, preferably two or three order(s) of magnitude below the lateral extension of the foil. Alternatively or in addition to a foil, the sealing foil may also include other types of sealing elements, for example, a simple coating, such as a parylene coating. The sealing foil may be connected, for example, as a continuous material to the end face and/or the radiation surface of the transducer core, for instance, by adhesion.

It is particularly preferred if the end face has at least one recess, especially at least one groove. Alternatively or in addition to a groove, other types of recesses may also be provided, such as blind hole-shaped recesses, slots, cut-outs or the like, the end face being preferably otherwise being embodied to be essentially flat. As will be explained below in greater detail, this at least one recess has the effect that gas occlusions, which may be created during the mounting of the ultrasonic transducer, are able to escape into this recess. The recess, in this instance, may also be connected to the hollow space via at least one connection, in particular at least one channel and/or a bore hole that runs in an axial direction of the ultrasonic transducer. A plurality of these connections may also be provided, for example, connections distributed at equidistant angular spacing over the circumference of the end face.

The ultrasonic transducer according to one or more of the embodiments, described above, has multiple advantages compared to the known ultrasonic transducers. In particular, in this way, an ultrasonic transducer may be produced, having a sealing foil on a side facing the measuring medium of the ultrasonic transducer, which, for example, not only extends beyond a transducer core, but also entirely or partially via an end face of the housing, such as an edge of the sleeve. The hollow-wall quality of the housing, in comparison to a simple housing and housing edge, makes possible a larger contact surface for the sealing foil, and with that, a considerably increased robustness, without leading to a delay in the production of the housing, such as in an extrusion process. The housing may be produced of a plastic material, in particular. The at least one hollow space may, for instance, include an essentially annularly encircling cored-out quality. The hollow space may particularly be situated on a side facing away from the foil, and may not be connected to the foil, or be connected via only one or a plurality of connections to the foil. One or a plurality of annularly situated hollowings-out or essentially radially running rib structures are also possible.

The coring out or the at least one hollow space may also be filled up entirely or partially, if required, using at least one acoustic damping element, for instance, an acoustic damping material, and thus at least reduce natural vibrations of the housing, for example, of the sleeve, for example, and disturbing structure-borne noise transmissions. This damping element or damping material may, for example, be fully or partially identical to a damping material which even in today's ultrasonic transducers is applied to the backside of the transducer core, in order to speed up the decaying of vibrations of the transducer core. For example, it may be a damping molding material. In this context, the damping molding material may hook mechanically into the hollow space, for instance, "clutch" into it, so that even in the case of poor adhesion to the housing, a displacement of the interior of the transducer in the direction of the measuring medium or in the opposite direction is impeded. A junction between the sealing foil and the housing is hereby protected additionally from mechanical stresses, for instance, from peeling stresses.

Furthermore, the at least one hollow space, for instance, the cored-out region, may be used for ventilation if, during the production process, vaporizing and/or decoupled plastics are applied to the interior space of the transducer, for instance, at high pressure. Moreover, the at least one hollow space may accommodate additional components, as shown above, particularly functional elements such as one, or a plurality of screening elements, such as an EMV screening sheet metal. Thus, on an overall basis, using the ultrasonic transducer according to the present invention, in one or more of the abovementioned embodiments, one may provide an ultrasonic transducer having an ultrasonic transducer housing, which makes possible functional improvements of the ultrasonic transducer and improved manufacturability in mass production.

DETAILED DESCRIPTION OF THE INVENTION

Figure 1:
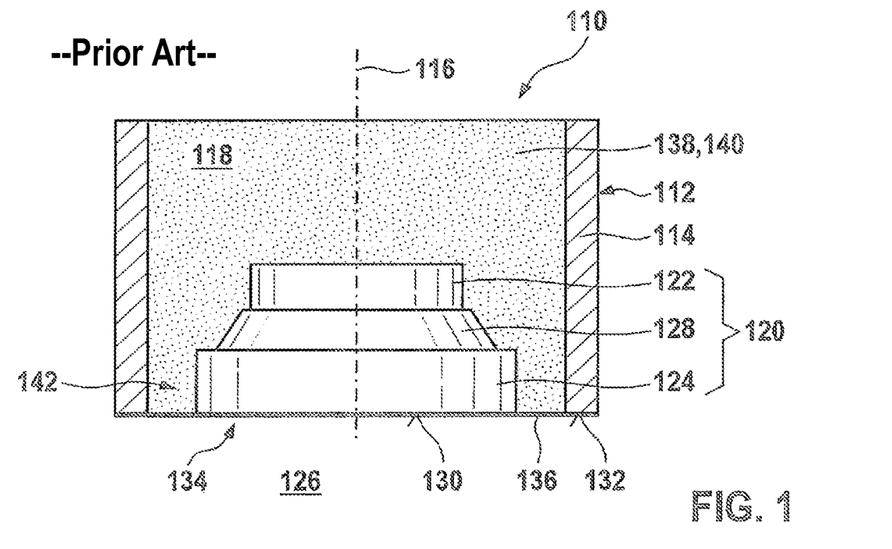
FIG. 1 shows a sectional view of a usual ultrasonic transducer.

In a sectional representation from the side, FIG. 1 shows an example of a usual ultrasonic transducer 110 in a greatly simplified specific embodiment. Ultrasonic transducer 110 includes a housing 112 having a housing wall 114. Housing 112 is only indicated symbolically in FIG. 1, and may be aligned axially symmetrical to an axis 116, for example. Housing 112 encloses an interior space 118, in which a transducer core 120 is accommodated. Transducer core 120 includes an electroacoustic transducer element 122, such as a piezoelectric transducer element, as well as an adaptation element 124 on the side of transducer core 120 facing a fluid medium. Adaptation element 124 is used for the impedance matching to the acoustic impedance of fluid medium 126, and may be developed according to the related art mentioned above. Furthermore, in the exemplary embodiment shown, between adaptation element 124 and electroacoustic transducer element 122, a compensating element 128 is optionally situated, whose thermal expansion lies between that of electroacoustic transducer element 122 and that of adaptation element 124, in order to compensate for, or at least reduce thermal stresses between these elements.

On its side facing fluid medium 126, transducer core 120 has a radiation surface 130. This is annularly surrounded by an end face 132 of housing 112, or housing wall 114. Housing 112 thus has on its side facing fluid medium 126 an opening 134, which is bordered by end face 132. In the exemplary embodiment shown, this opening is closed by a sealing foil 136, which may be connected over a large surface to end face 132, for example, and/or radiation surface 130, for instance, by adhesion.

In the exemplary embodiment shown, interior space 118 is further filled up with a damping element 138, such as a damping extrusion compound 140.

Thus, FIG. 1 shows a basic design of an ultrasonic transducer 110 having a, for instance, simple cylindrical sleeve as housing 112, which corresponds to the related art. A piezoceramic of electroacoustic transducer element 122 may be connected, in this instance, via an adhesion and/or a compensating element 128, that may be designed as a compensating layer, for example, to adaptation element 124 used for the impedance matching, which simplifies a sonic coupling with fluid medium 126. After the transmission process, in order to limit in time the reverberation of electroacoustic transducer element 122, interior space 118 may be filled up with damping extrusion compound 140.

Various modifications of the transducer design according to FIG. 1 are known from the related art, which are basically also used within the scope of the present invention, and may be modified according to the present invention. These optional embodiments relate to adaptation element 124, for example, and/or compensating element 128. The compensating element, for example, such as the compensating layer, may be used when, on the other hand, a large temperature measuring range is to be covered, and on the other hand, when rapid temperature changes occur in the application, and when a comparatively large electroacoustic transducer element 122 is to be used. The latter may be a thick piezo disk, for example, such as a piezo disk of 8×2 mm, which, because of its flexural strength, has a comparatively low temperature sensitivity, but instead reacts sensitively to mechanical stresses based on thermal expansion of the adaptation layer. If, however, a slightly larger temperature sensitivity is tolerated, a thinner piezo disc, such as measuring 8×0.2 mm, may optionally also be used without a compensating layer and/or without compensating element 128.

Adaptation element 124 may be embodied according to the related art, for example. On this matter, reference may be made, for example, to the related art cited above. Epoxy/glass hollow sphere compounds may be used, for example, as is described in European patent document EP 0 766 071 B1, for instance. Other types of adaptation elements are basically possible, however, for instance, adaptation element 124 having porous plastics, such as porous polyimides. In these cases, a compensating layer 128 may be required, for example, to close the pores, especially in order to make possible a subsequent adhesion.

Further modifications relate to the embodiment of the sealing of ultrasonic transducer 110, for example, for the improvement of resistance to chemicals, moisture or aggressive media. For this purpose, sealing foil 136 is provided which, as shown above, may also include a coating, optionally, alternatively or in addition to a foil. Such sealing foils 136 are basically known from JP 2002 214008 A or from JP 2002 135894 A, for example. Sealing foil 136 may be made up of a polyimide and/or a thermoplastic material such as PEEK (polyetheretherketone) or have such a material in it. However, other designs are basically also possible.

Figure 2:
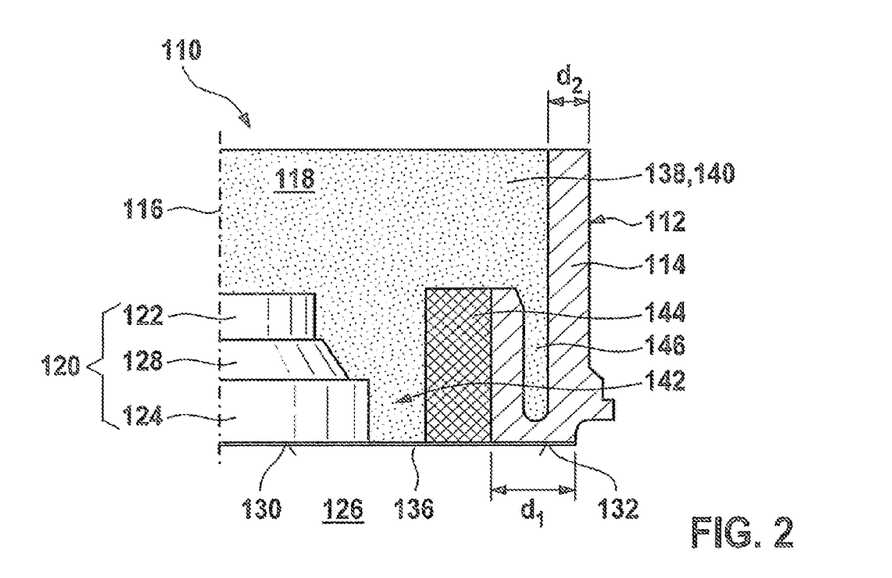
FIG. 2 shows a first exemplary embodiment of an ultrasonic transducer according to the present invention.

Furthermore, in an interspace 142 between transducer core 120 and housing 112, at least one decoupling element may be provided, which is not shown in FIG. 1, and is designated in FIG. 2 by reference numeral 144. This decoupling element may, for instance, be designed as a structural part or also simply as a decoupling material, which, for instance, may be poured into interspace 142 and/or inserted in another manner.

It is pointed out that ultrasonic transducer 110, shown in FIG. 1 and corresponding to the related art, which has just been described in detail with its modifications and possible embodiments, may also basically be used within the scope of the present invention. However, as will be described in greater detail below, in that case, housing 112 is replaced by a housing 112 according to the present invention, having the features, shown in the introduction and explained in exemplary fashion more closely in the following, of such a housing 112.

A first exemplary embodiment of an ultrasonic transducer 110 according to the present invention is shown in FIG. 1 in a sectional view. This ultrasonic transducer 110 may, first of all, largely correspond to ultrasonic transducer 110 according to FIG. 1, so that we may also refer in an exemplary manner to the description of FIG. 1. In FIG. 2, by contrast to FIG. 1, and as described above, an example is shown in which a decoupling element 144 is provided optionally in interspace 142, between transducer core 120 and housing wall 114. However, other designs are basically also possible.

One difference between the exemplary embodiment, according to the present invention, in FIG. 2 and the related art, according to FIG. 1, is that housing wall 115 has at least one hollow space 146. In the exemplary embodiment shown, this hollow space is preferably formed by having a lower edge of housing wall 114 crimped or flanged over inwards, into interior space 118. Thereby, end face 132, of housing wall 114, that faces fluid medium 126 is preferably developed to be wider, or has a greater thickness (designated by $d_1$ in FIG. 2), than housing wall 114 outside hollow space 146. The flanging may extend, for example, so far into interior space 118 that hollow space 146 encloses entire transducer core 120 in an annular manner.

Thus, FIG. 2 shows an exemplary embodiment of ultrasonic transducer 110 according to the present invention, in which the wall thickness of the sleeve of housing 112 has been increased in order to increase end face 132, which is able to be used as the contact surface of sealing foil 136. Because of that, an increased firmness is imparted to the intersection between housing 112 and sealing foil 136. Hollow space 146 is embodied as being cored-out, for example. Hollow space 146, on the one hand, avoids a delay in, or rather, after an optional extrusion process, by which housing 112 is able to be produced. As a function of a viscosity of the not yet completely cross-linked damping material of damping element 138, which in first place is supposed to damp electroacoustic transducer element 122, such as the piezo, the cored-out state, on the other hand, was developed to the extent that this damping material is able to flow into the corresponding hollow space 146. Structure-borne noise vibrations of the sleeve of housing 112 may be damped by these measures. The filling by damping element 138, such as damping extruding compound 140, that is largely free of undesired air occlusions, may be achieved particularly by vacuum casting. The air occlusions that would otherwise result, in the case of frequent temperature changes, would, as a rule, lead to high stresses, which, in the final analysis, age ultrasonic transducer 110 prematurely. Decoupling element 144 may optionally be provided, for instance, an additional decoupling using silicone foam.

The latter may be also be enclosed by the damping material of damping extruding compound 140, which may include, for example, silicone, epoxyurethane or polyurethane, for instance, foamed and/or having added fillers.

Figure 3A:
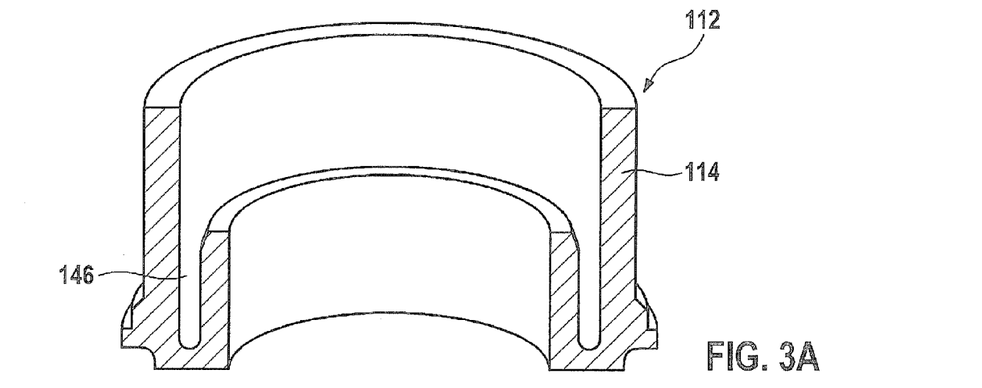
FIGS. 3a-3c show exemplary embodiments of a plurality of housings for use in an ultrasonic transducer according to the present invention.
Figure 3B:
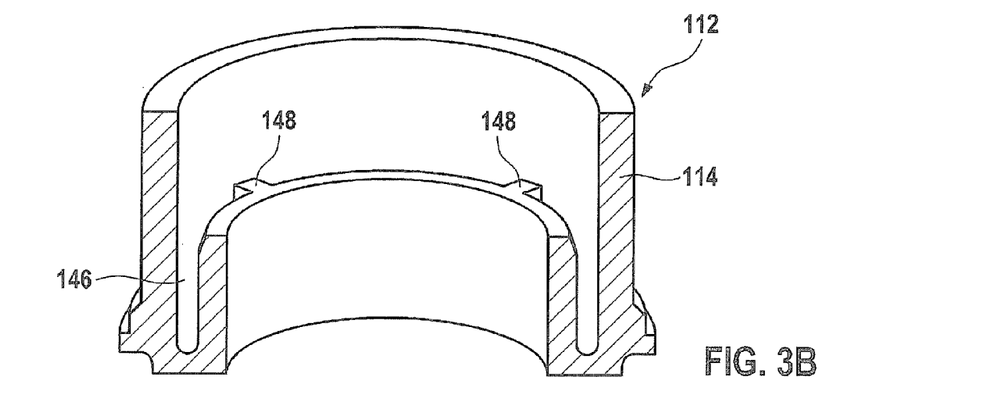
Figure 3C:
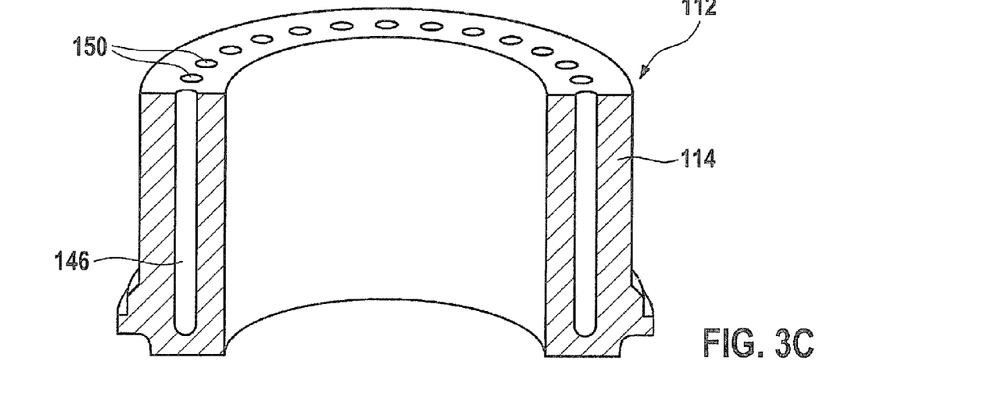

FIGS. 3A to 3C show different embodiments of housing 112 or housing wall 114, which may also be used in the exemplary embodiment according to FIG. 2. In each case, a perspective sectional view is shown, in this instance. The embodiment according to FIG. 3A essentially corresponds to the embodiment of the housing used in FIG. 2. In FIG. 3B a variant is shown in which the cored-out gap, which forms hollow space 146, it is true, is executed in an essentially enciling manner, but it is interrupted by additional, radially running support ribs 148. In the exemplary embodiment according to FIG. 3C, the hollow-wall quality is embodied in the form of annularly arranged bore holes 150, which extend in the axial direction and which may be positioned equidistantly.

Figure 4A:
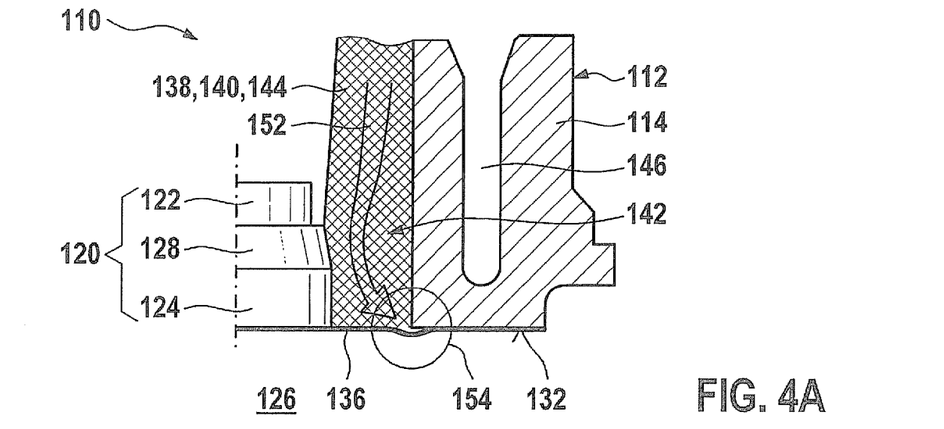
FIGS. 4A-4C show various embodiments of end faces of the housing in an ultrasonic transducer according to the present invention.
Figure 4B:
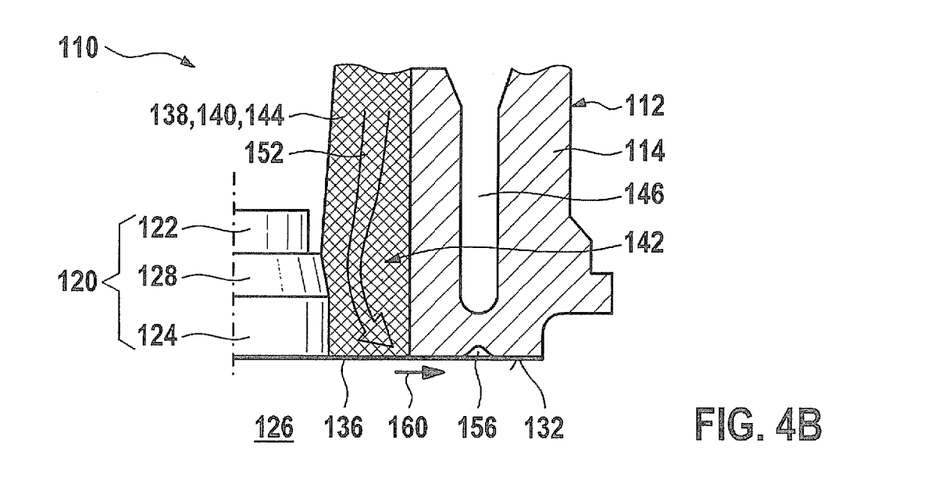
Figure 4C:
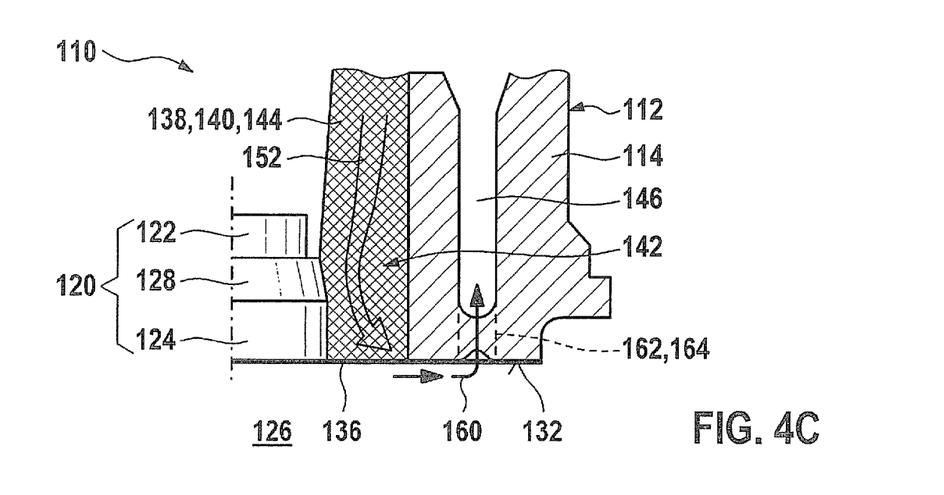

Various detailed views of end face 132 are shown in various embodiments in FIGS. 4A to 4C. In this context, a situation is shown during which damping element 138 and/or decoupling element 144, which may also be entirely or partially identical, are introduced into interspace 142, for instance, by a casting process and/or a spraying process. In this instance, the arrow designated by reference numeral 152 shows a flow direction of the materials used. It should be pointed out that other processes for inserting elements 138, 140 or 144 may basically also be used. The embodiment shown should only explain processes in the region of interspace 142 facing fluid medium 126 and explain the stressing of sealing foil 136 in this region. The area, in which this sealing foil 136 is most greatly stressed as a rule, is designated symbolically by reference numeral 154 in FIG. 4A. In this region, the connection of sealing foil 136 with the sleeve of housing 112 reacts particularly sensitively to thermally conditioned expansions in the interior of the transducer. In particular, in this region, air occlusions should usually be avoided which, during temperature changes and/or pressure changes, are able to lead to great volume changes and correspondingly high, localized forces. Above all, in methods in which the material of decoupling element 144 and/or the material of damping element 138 is sprayed on, in a spraying process at high pressure and high temperature onto sealing foil 136 and/or the sleeve of housing 112, for instance, using flow direction 152 of the material flow, above all at points of the flowing together of materials, with respect to the spray-on points, there exists the danger of small air occlusions which, even during the spraying process, are able to lead to local pressure and temperature increases (so-called burners). These occlusions may be created even in response to evacuation, because of the still-present residual pressure, or caused by targeted air or gas admixtures that are used, as a rule, to improve the acoustical decoupling properties of the materials used. In order to defuse this situation, an exemplary embodiment is shown in FIG. 4B, in which end face 132 has at least one recess 156. This recess 156 in end face 132 may basically also be used in embodiments of housings which do not have hollow space 146 according to the present invention, but it is advantageous in connection with this hollow space 146, as will be explained below. In the exemplary embodiment in accordance with FIG. 4B, recess 156 is embodied in the form of a groove. This may be a concentric groove which, for instance, has a circular course in end face 132. Into this at least one recess, the corresponding gas occlusions are able to destress themselves after a preceding tool evacuation. The air occlusions are able to be displaced into the destressing volume of groove or recess 156, through very small leakage cross sections between sealing foil 136 and housing 112, which in FIG. 4B and in FIG. 4C is symbolized by arrow 160. The sprayed-in material, in contrast, remains staying at the junction between sealing foil 136 and housing wall 114. At the same time, the production process may be designed so that sealing foil 136 is optionally coated with adhesive, which fully hardens only during or after the spraying process, and thus closes again the leakage cross sections used before for the air.

One further design of the exemplary embodiment according to FIG. 4B uses the presence of hollow space 146 in a targeted manner. In this design, the at least one recess 156 may be connected in end face 132 via at least one connection 162 to hollow space 146. This at least one connection 162 may, for instance, include a plurality of channels 164, which run in the axial direction, for example. Via these channels 164, recess 156 may, for example, be connected to a cored-out space that forms hollow space 146, so that excess air is able to exit, or also a slight quantity of exiting decoupling material and/or damping material are able to rise up within the cored-out space.

Figure 5:
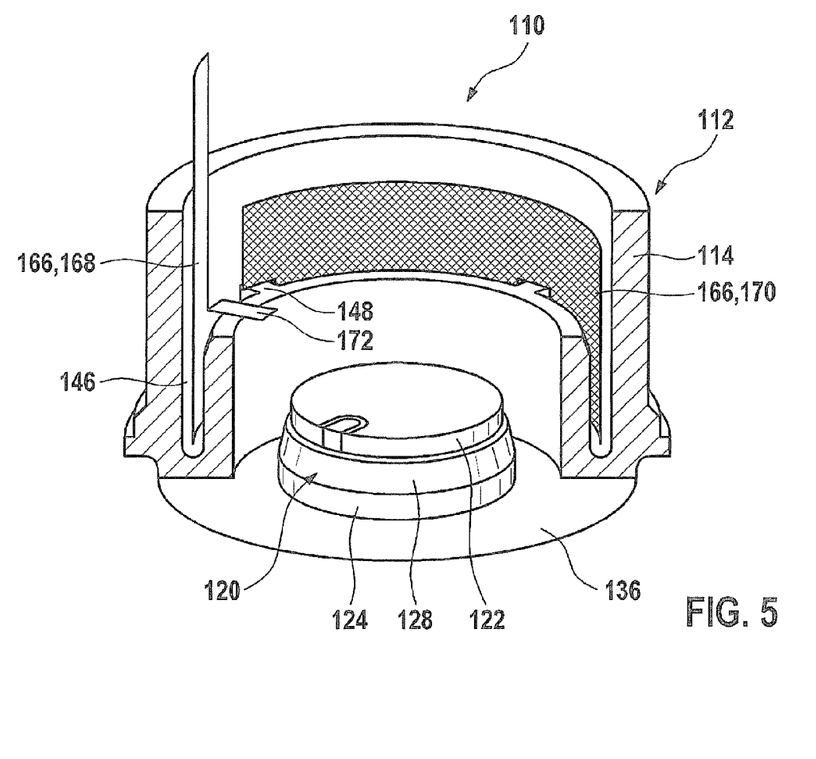
FIG. 5 show an exemplary embodiment having in addition a functional element accommodated in a hollow space of the housing.

In a perspective sectional view, finally, FIG. 5 shows schematically an additional exemplary embodiment of ultrasonic transducer 110 according to the present invention. Ultrasonic transducer 110, in turn, corresponds, for instance, to the design according to FIG. 2, a housing wall 114 of the design of FIG. 3B being used, however. However, other designs are basically also possible.

In the exemplary embodiment according to FIG. 5, it is shown that, in hollow space 146, one or more functional elements 166 may also be fully or partially accommodated. These functional elements 166 may include, for example, the already mentioned decoupling element 144 and/or damping element 138, as is indicated in FIG. 2 in exemplary fashion. In FIG. 2, hollow space 146 is optionally filled up with damping element 138. On the other hand, in the exemplary embodiment according to FIG. 5, as functional element 166, an electric contact 168 is provided for the electrical contacting of electroacoustic transducer element 122 or, alternatively or additionally, a screening element 170, such as an EMC screening (EMC: electromagnetic compatibility). Electric contact 168 may be designed as a contact pin, for example. It may have one or more connecting elements 172, in order to connect it to housing 112. These connecting elements 172 may include latching hooks, for example, which, in the case of the use of sheet metal parts are able to be pressed into them. Connecting elements of screening element 170 may also be provided. Alternatively or additionally to functional elements 166 mentioned, additional functional elements 166 may be fully or partially accommodated in hollow space 146.

The exemplary embodiments of ultrasonic transducer 110, shown in FIGS. 2 through 5, represent only some possible embodiments of ultrasonic transducer 110. Ultrasonic transducer 110 may particularly be used in ultrasonic flow meters (UFM). In particular, ultrasonic transducer 110 may be used in motor vehicle internal combustion engines, especially in the field of commercial motor vehicles. Alternative application fields are sensors for gases or liquids, for example, also for process control, for instance, in process control as distance sensors, as fluid-level sensors or as flow sensors, such as in the chemical and/or the pharmaceutical industry. Additional application possibilities are medicinal technology, such as in breathing gas monitoring and/or energy technology, such as in heat counters in power stations or in household applications.

What is claimed is:

1. An ultrasonic transducer for use in a fluid medium, comprising:
    at least one housing shaped as a sleeve and having at least one interior space; and
    at least one transducer core accommodated in the interior space and having at least one electroacoustic transducer element;
    wherein the housing has a housing wall at least partially enclosing the transducer core, the housing wall having at least one hollow space, wherein the hollow space of the housing wall is one of: (i) formed by a flanging of the housing wall towards the interior space of the housing; (ii) subdivided by at least one rib extending in the axial direction of the ultrasonic transducer; (iii) a bore hole extending in the axial direction of the ultrasonic transducer; (iv) a cored-out region extending essentially annularly around the interior space; and (v) formed by at least one radially extending rib structure.

2. The ultrasonic transducer as recited in claim 1, wherein the hollow space is completely separated from outside region of the housing.

3. The ultrasonic transducer as recited in claim 1, wherein multiple hollow spaces are distributed essentially uniformly over the circumference of the housing wall.

4. The ultrasonic transducer as recited in claim 1, wherein the hollow space is configured in such a way that a thickness of the housing wall varies over different regions of the housing by a factor of four, at a maximum.

5. The ultrasonic transducer as recited in claim 1, wherein the hollow space is configured in such a way that an end face of the housing facing the fluid medium has a greater thickness in the radial direction of the ultrasonic transducer than an average wall thickness of the housing wall.

6. The ultrasonic transducer as recited in claim 1, wherein the hollow space is at least partially filled with a functional element which is different from the material of the housing.

7. The ultrasonic transducer as recited in claim 6, wherein the functional element includes at least one of: a damping element having at least one damping material to suppress structure-borne noise transmissions; a contact element for electrical contacting of the electroacoustic transducer element; a mounting element for mounting the contact element for electrically contacting the electroacoustic transducer element; and a screening element for screening the interior space from electromagnetic effects.

8. The ultrasonic transducer as recited in claim 1, wherein:
    the housing has at least one opening facing the fluid medium, the opening being at least partially enclosed by an end face of the housing wall;
    at least one radiation surface of the transducer core is situated within the opening; and
    the opening and the end face being at least partially covered by at least one sealing foil.

9. The ultrasonic transducer as recited in claim 8, wherein the end face has at least one recess.

10. An ultrasonic transducer for use in a fluid medium, comprising:
    at least one housing shaped as a sleeve and having at least one interior space; and
    at least one transducer core accommodated in the interior space and having at least one electroacoustic transducer element;

wherein the housing has a housing wall at least partially enclosing the transducer core, the housing wall having at least one hollow space, and the housing has at least one opening facing the fluid medium, the opening being at least partially enclosed by an end face of the housing wall, wherein;

at least one radiation surface of the transducer core is situated within the opening; and the opening and the end face being at least partially covered by at least one sealing foil, wherein the end face has at least one recess; and wherein the recess is connected to the hollow space via at least one channel extending in an axial direction of the ultrasonic transducer.

* * * * *